US00PP12214P2

(12) United States Plant Patent
Glicenstein

(10) Patent No.: US PP12,214 P2
(45) Date of Patent: Nov. 20, 2001

(54) CHRYSANTHEMUM PLANT NAMED 'ZESTY YOJEAN'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/478,444

(22) Filed: Jan. 6, 2000

(51) Int. Cl.[7] ..... A01H 5/00
(52) U.S. Cl. ..... Plt./287
(58) Field of Search ..... Plt./287, 292

(56) References Cited

PUBLICATIONS

Datta, 1994, "Sensitivity of mutant genotypes of chrysanthemum to gamma rays", J. Nuclear Agric Biol., 23(4):251–254.*
"Mutation studies on chrysanthemum", NBRI Newsletter, 1989, 16(1):2–3.*
Datta, 1991, "Evaluation of recurrent irradiation on vegetatively propagated ornamental chrysanthemum", J. Nuclear Agric. Biol., 20(2):81–86.*
Banerji, et al., 1990, "Induction of somatic mutation in chrysanthemum cultivar 'Anupam'", J. Nuclear Agric. Biol., 19:252–256.*
Datta, 1985, "Gamma ray induced mutant of a mutant of chrysanthemum", J. Nuclear Agric. Biol., vol. 14:131–133.*
Gosling, ed., 1979, "The Chrysanthemum Manual—6$^{th}$ edition", The National Chrysanthemum Society, Essex Telegraph Press, Ltd., London, pp. 329–336.*
Broertjes, et al., 1978, "Application of Mutation Breeding Methods In the Improvement of Vegetatively Propagated Crops", Elsevier Sci. Pub. Co., New York, pp. 162–175.*
Gupta, et al., 1978, "Mutation breeding of chrysanthemum. II. Detection of gamma ray induced mutants in vM2", J. Nuclear Agric. Biol. 7(2):50–54.*
Glazurina, et al., 1977, "Use of artificial mutagenesis in the breeding of flower crops", Cytology and Genetics, vol. 11(3):42–45.*
Das, et al., 1977, "Improvement of some vegetatively propagated ornamentals by gamma radiation", Indian J. Horticulture, 34(2):169–174.*
Dowrick, et al., 1966, "The induction of mutations in chrysanthemum using X– and gamma radiation", Euphytica, 15:204–210.*
Broertjes, 1966, "Mutation breeding of chrysanthemums", Euphytica, 15:156–162.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Zesty Yojean', characterized by its uniformly mounded plant habit; freely branching growth habit; uniform and early flowering; decorative-type inflorescences that are about 4.5 cm in diameter; attractive coral peach ray florets; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and hereinafter referred to by the cultivar name Zesty Yojean.

The new Chrysanthemum is a product of a mutation induction breeding program conducted by the Inventor in Fort Myers, Fla., and Salinas, Calif. The objective of the program is to create new Chrysanthemum cultivars with inflorescences with desirable inflorescence forms, attractive floret colors and good garden performance.

The new Chrysanthemum originated by exposing unrooted cuttings of the Chrysanthemum cultivar Jean, disclosed in U.S. Plant Pat. No. 10,901, to gamma-ray radiation in Feb., 1996, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in July, 1996. The selection of this plant was based on its desirable inflorescence form, attractive ray floret color and excellent garden performance.

Asexual reproduction of the new cultivar by terminal cuttings taken in a controlled environment in Salinas, Calif. has shown that the unique features of this new Chrysanthemum are stable and reproduced true to type in successive generations.

SUMMARY OF THE INVENTION

The cutlivar Zesty Yojean has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zesty Yojean'. These characteristics in combination distinguish 'Zesty Yojean' as a new and distinct cultivar:

1. Uniformly mounded plant habit.
2. Freely branching, dense, full plants.
3. Uniform and early flowering.
4. Decorative-type inflorescences that are about 4.5 cm in diameter.

5. Attractive coral peach-colored ray florets.
6. Numerous inflorescences per plant.
7. Excellent garden performance.

Compared to plants of the parent cultivar, Jean, plants of the new Chrysanthemum flower a few days later under artificially-manipulated photoperiodic conditions and differ in ray floret color as plants of 'Jean' have light pink-colored ray florets.

BRIEF DESCRIPTION OF THE PHOTOGRAPHS

The ccompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which more accurately describe the actual colors of the new Chrysanthemum.

The photograph at the top of the sheet comprises a top perspective view of a typical flowering plant of 'Zesty Yojean'.

The photograph at the bottom of the sheet comprises a close-up view of typical inflorescences of the cultivar 'Zesty Yojean'.

DETAILED BOTANICAL DESCRIPTION

In the following description, color references are made to The Royal Horticultural Society Colour Chart except where general terms of ordinary dictionary significance are used. The following observations and measurements describe plants grown in Pendleton, S.C., under conditions which approximate those generally used in commercial garden Chrysanthemum production. One rooted cutting was planted in a 15-cm container on Jul. 26, 1999 and plants were grown under natural season conditions. Plants were not pinched, that is, the terminal apex was not removed to enhance branching. Measurements and numerical values represent averages for typical flowering plants.

Botanical classification: *Dendranthema grandiflora* cultivar Zesty Yojean.

Commercial classification: Decorative-type garden chrysanthemum.

Parentage: Induced mutation of *Dendranthema grandiflora* cultivar Jean, disclosed in U.S. Plant Pat. No. 10,901.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle; mounded plant form. Stems initially upright, then outwardly spreading giving a uniformly mounded appearance to the plant. Freely branching with lateral branches potentially developing at every node.

*Plant height.*—About 28 cm.

*Plant spread.*—About 39 cm.

*Stems.*—Texture: Pubescent. Color: 146A; with anthocyanin, close 59A.

*Foliage description.*—Leaf arrangement: Alternate. Length: About 4.5 cm. Width: About 4.1 cm. Apex: Cuspidate to mucronate. Base: Mostly truncate. Margin: Palmately lobed, sinuses mostly parallel. Texture: Upper surface sparsely pubescent; lower surface moderately pubescent. Veins prominent on lower surface. Petiole length: About 1.7 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative-type inflorescence form with spatulate-shaped ray florets. Inflorescences borne on terminals above foliage, arising from leaf axils. Disk and ray florets arranged acropetally on a capitulum. About 144 inflorescences per plant.

*Flowering response.*—Under natural season conditions, plants flower in the autumn about 66 days after planting.

*Inflorescence bud.*—Height: About 5 mm. Diameter: About 7 mm. Color: 137A.

*Inflorescence size.*—Diameter: About 4.5 cm. Depth (height): About 2.1 cm. Diameter of disc: About 3 mm.

*Ray florets.*—Shape: Spatulate; concave. Length: About 2 cm. Corolla tube: About 6.5 mm. Width: About 6 mm. Apex: Minutely dentate. Margin: Entire. Texture: Smooth, glabrous, satiny; iridescent. Orientation: Initially upright, then perpendicular to the peduncle. Number of ray florets per inflorescence: About 194. Color: When opening, upper surface: Initially green, close to 144A; then close to 161A with anthocyanin, close to 58A, overtones. When opening, lower surface: Initially green, close to 144A; then close to 164D with anthocyanin, close to 58A, overtones. Anthocyanin coloration more pronounced towards apex. Opened inflorescence, upper surface: Close to 161D with anthocyanin, close to 58A, overtones. Anthocyanin coloration more pronounced towards apex. Opened inflorescence, lower surface: Close to 161D with anthocyanin, close to 58A, overtones. Anthocyanin coloration more pronounced towards apex.

*Disc florets.*—Shape: Tubular, apex dentate. Length: About 6 mm. Width: Apex: About 1.5 mm. Base: About 1 mm. Number of disc florets per inflorescence: About 12 or less. Color: Immature: 154A. Mature: Apex: 12A. Base: Whitish green.

*Peduncle.*—Aspect: Flexible, angled about 55 to 60° to the stem. Length: First peduncle: About 7.5 cm. Fourth peduncle: About 11.8 cm. Diameter: About 2 mm. Texture: Pubescent. Color: Darker than 144A.

*Reproductive organs.*—Androecium: Present on disc florets only. Anther color: 12A. Pollen: Scarce. Pollen color: 14A. Gynoecium: Present on both ray and disc florets.

*Seed.*—Seed production has not been observed.

Disease resistance: Plants of the new Chrysanthemum have not been shown to be resistant to pathogens common to Chrysanthemums.

It is claimed:

1. A new and distinct cultivar of Chrysanthemum plant named 'Zesty Yojean', as illustrated and described.

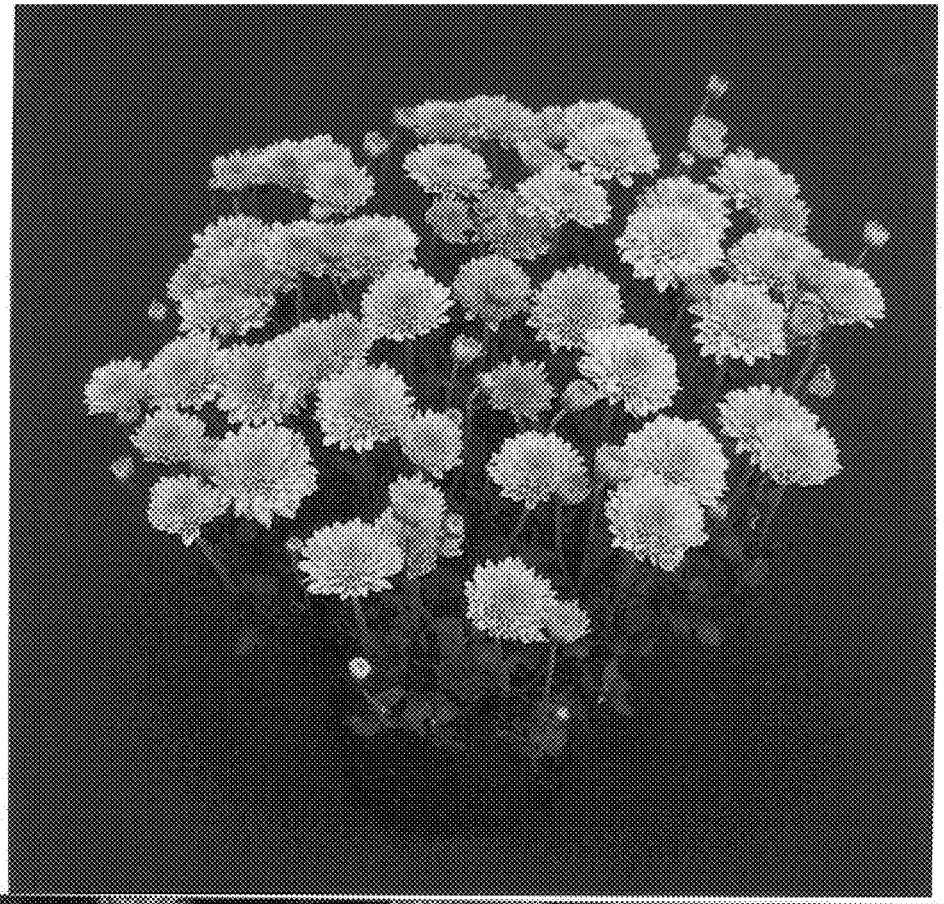
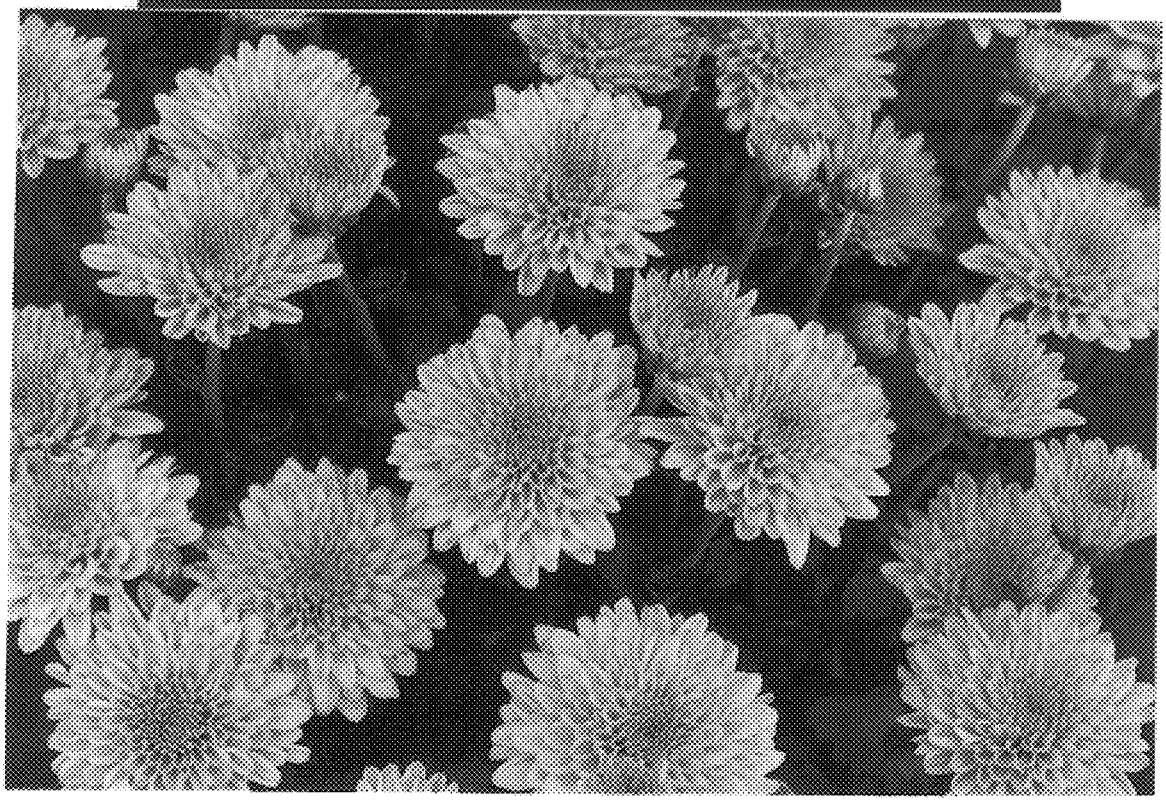

* * * * *